United States Patent [19]

Richard

[11] Patent Number: 5,135,721
[45] Date of Patent: Aug. 4, 1992

[54] STERILIZATION AND COATING APPARATUS

[75] Inventor: Daniel D. Richard, Sedona, Ariz.

[73] Assignee: Net/Tech International, Inc., Baldwin, N.Y.

[21] Appl. No.: 467,056

[22] Filed: Jan. 18, 1990

[51] Int. Cl.$^5$ .......................... B05B 3/00; B05C 3/09; A61L 2/18; A61L 2/20

[52] U.S. Cl. .................................... 422/111; 118/300; 118/318; 250/455.11; 422/1; 422/110; 422/116; 422/292; 422/300; 425/2; 425/269; 427/2; 427/155

[58] Field of Search ...................... 422/1, 40, 292, 300, 422/22, 23, 24, 28, 110, 111, 116; 118/300, 318; 425/2, 117, 129.1, 269, 275; 249/55; 427/2, 155; 250/455.1

[56] References Cited

U.S. PATENT DOCUMENTS 4,521,365  6/1985  Kurtz ..................... 425/269 X
4,670,010  6/1987  Dragone ................. 422/292 X
4,688,585  8/1987  Vetter ..................... 134/56 R Primary Examiner—Jill A. Johnston
Attorney, Agent, or Firm—R. Neil Sudol; Henry D. Coleman

[57] ABSTRACT

A sterilization apparatus comprises a housing provided with an opening through which an object may be inserted, and an ultraviolet radiation generator at least partially inside the housing for irradiating with bactericidal radiation an object inserted into the housing through the opening. A liquid spraying mechanism or gas injection mechanism is disposed at least partially inside the housing for applying to the inserted object a sterilizing agent. A coating or cover forming mechanism is also provided at least partially inside the housing for forming on the inserted object a protective covering. A control unit controls the activation of the radiation generator, the sterilizing mechanism and the coating mechanism.

62 Claims, 5 Drawing Sheets

STERILIZATION AND COATING APPARATUS

BACKGROUND OF THE INVENTION

This invention relates to a sterilization apparatus. This invention also relates to an apparatus for providing a protective coating or covering on on object such as a hand. More particularly, the present invention relates to a combination sterilizing and gloving apparatus. Such a sterilizing and coating or gloving apparatus is useful in the medical field, particularly for sterilizing and protecting surgeons' hands prior to surgery. The sterilization apparatus, the gloving apparatus and the combination apparatus have applications in other fields as well, such as in the food service industry.

In preparing for surgery, surgeons must scrub their hands with a sterilizant or bacteriocidal agent. Then, they have assistants help them put on sterilized latex gloves. This is a time consuming process and expensive in that it requires the help of assistants who might otherwise be occupied in surgical preparations.

OBJECTS OF THE INVENTION

An object of the present invention is to provide a sterilizing apparatus which facilitates cleaning and sterilizing one's hands.

Another object of the present invention is to provide such an apparatus which is essentially entirely automatic.

Another, more particular, object of the present invention is to provide such an apparatus which is easily activated.

Yet another object of the present invention is to provide an apparatus for automatically providing a protective coating on an object, particularly for forming or putting gloves on a surgeon's hands.

Another particular object of the present invention is to provide such a coating or glove forming apparatus which is easily activated.

An additional object of the present invention is to provide a combined sterilizing and coating apparatus, or more specifically, a combined sterilizing and gloving apparatus.

Yet a further object of the present invention is to provide such a combination apparatus which utilizes several different sterilizing techniques to maximize the effectiveness of the sterilization.

SUMMARY OF THE INVENTION

A sterilization apparatus in accordance with the present invention comprises a housing provided with an opening through which an object may be inserted, and a first device at least partially inside the housing for irradiating with bacteriocidal radiation an object inserted into the housing through the opening. A second device is disposed at least partially inside the housing for applying to the inserted object a sterilizing agent, while a third device is provided at least partially inside the housing for forming on the inserted object a protective covering. A control unit is provided for controlling the activation of the first device, the second device, and the third device.

Pursuant to another feature of the present invention, the irradiation device includes an assembly for generating and emitting ultraviolet radiation. It is advantageous if the irradiation device further includes components for modifying the frequency and intensity of the emitted ultraviolet radiation.

Pursuant to an additional feature of the present invention, the sterilizing agent is an atomized liquid containing a bacteriocidal substance. The sterilizing liquid may be sprayed onto the object to be sterilized. Alternatively, the sterilizing agent may be contained in a reservoir into which the object may be dipped. The reservoir may be stored in an open tank movable between a storage position and an in-use position at the location of the object to be sterilized.

Pursuant to a particular embodiment of the present invention, the sterilizing agent is gaseous. A particularly effective gaseous sterilant, commonly used in other applications, is ethylene oxide. That gas is capable of killing virtually any unicellular life form, including bacteria, viruses, and spores, as well as fungi and mold. A similarly effective gaseous sterilant is propylene oxide. Other gases which can be used, although not as effective, include gaseous alcohol and ozone.

A gaseous sterilant is preferable to a non-gaseous sterilant inasmuch as the gaseous sterilant easily penetrates to cracks and crevices in which micro-organisms reside. Because liquids do not penetrate so readily to miniscule locations, use of liquids frequently require an additional mechanical action, i.e., scrubbing, to be as effective as the gaseous sterilants.

A drawback to certain gaseous sterilants, however, particularly ethylene oxide, is that they are considered dangerous to inhale. This danger can be effectively met, in accordance with the present invention, by rapidly and efficiently removing the gas from the sterilization chamber (the housing) and storing the gas in a sealed container.

In accordance with a particular embodiment of the present invention, the covering device includes an applicator assembly for applying to the inserted object a liquid substance which upon drying solidifies into a thin flexible film. A blower, heater and/or infrared radiation generator or other dryer is preferably provided at least partially inside the housing for drying the liquid substance upon application thereof to the inserted object.

In order to facilitate the formation on the inserted object of a protective layer which is substantially nonporous, several cycles of applying and then drying the liquid are performed.

The liquid coating substance is, in one embodiment of the invention, sprayed onto the inserted object. In another, alternative, embodiment of the invention, the liquid substance is held in a container to enable immersion of the object into the liquid substance. In the latter case, the inserted object and the container are moved relative to one another to effectuate the immersion of the object in the liquid coating substance.

The liquid coating substance may be liquid latex, which is presently used to make latex gloves. In the immersion process, the object is first immersed in a coagulant such as zinc nitrate or another substance well known in the art. The object is then immersed in the latex and, upon removal from the latex bath, again immersed in the coagulant.

Upon the formation of a layer of the liquid coating substance, the layer may be dried by air from a blower. Alternatively or additionally, the layer of the liquid coating substance may be heated or subjected in infrared radiation.

The various devices of the sterilizing apparatus are activated by the control unit. More particularly, the control unit may take the form of a microprocessor preprogrammed to control the timing of the various processes, including the generation of the bacteriocidal radiation, the application of the sterilizing agent and the formation of the protective coating or layer. More specifically, the control unit activates the blower, heater and/or infrared radiation generator or other dryer upon application of a liquid sterilizing agent to the object and upon application of the liquid coating substance to the object.

In a particular application of the present invention, the object to be sterilized and protected is a hand (e.g., the hand of a surgeon). The covering or coating device includes (a) an assembly for forming a pair of glove portions, (b) a mechanism for positioning the glove portions about a hand inserted into the apparatus, thereby substantially enclosing the hand, and (c) an assembly for joining the glove portions to one another to form the protective covering. More specifically, the assembly which forms the glove portions includes a pair of mold halves and a sprayer or other device for depositing a substantially nonporous coating of a flexible material on the mold halves. In addition, the positioning mechanism includes components for moving the mold halves towards one another.

In a particular embodiment of the present invention, a housing stores a plurality of preformed gloves rolled up into opened configurations facilitating the insertion of finger tips into the finger portions of the gloves. A mechanism is provided for rolling the rolled up gloves down about a pair of hands upon insertion of the finger tips into the rolled up gloves. The rolling mechanism may include a flexible, expandable ring translatable in a direction from the fingertips towards the wrist of a hand which has been inserted into the apparatus.

In yet another, alternative, embodiment of the present invention, the preformed gloves are oversized, a device being provided for heat shrinking the oversized gloves about hands inserted thereinto.

Pursuant to a particular feature of the present invention, the control unit is user responsive. The apparatus is activated, for example, by voice command. In that case, the apparatus is provided with an acousto-electric transducer (microphone), as well as software and known hardware for recognizing different spoken sounds. The control unit may activate different components of the sterilizing and gloving apparatus, depending on which key words are spoken. Upon detecting a predetermined word or other sound, the control unit may activate the irradiating device, the liquid coating applicator and the covering device in a predetermined sequence.

In accordance with the present invention, the various components of the apparatus may be included in different combination. One such combination includes the irradiation device and the device for applying a sterilizing agent (liquid or gas). Another combination includes the irradiation device and the device for providing a protective coating or layer. Yet another combination includes the the device for applying a sterilizing agent (liquid or gas) and the device for providing a protective coating or layer. Each such combination includes a control unit such as a microprocessor for initiating, sequencing, and timing the various operations. In addition, the combinations preferably all include an activation mechanism or circuit for enabling control of the apparatus by the user.

An apparatus in accordance with the present invention is automatic and user controlled. The device thereby facilitates cleansing (sterilizing) operations. In addition, gloves are applied automatically, without the need for additional, assisting personnel.

An apparatus in accordance with the present invention is useful in any industry or profession which requires sterilized hands or instruments or a protective covering such as gloves. Hospitals and restaurants are particularly benefited by the invention.

DETAILED DESCRIPTION

Figure 1:
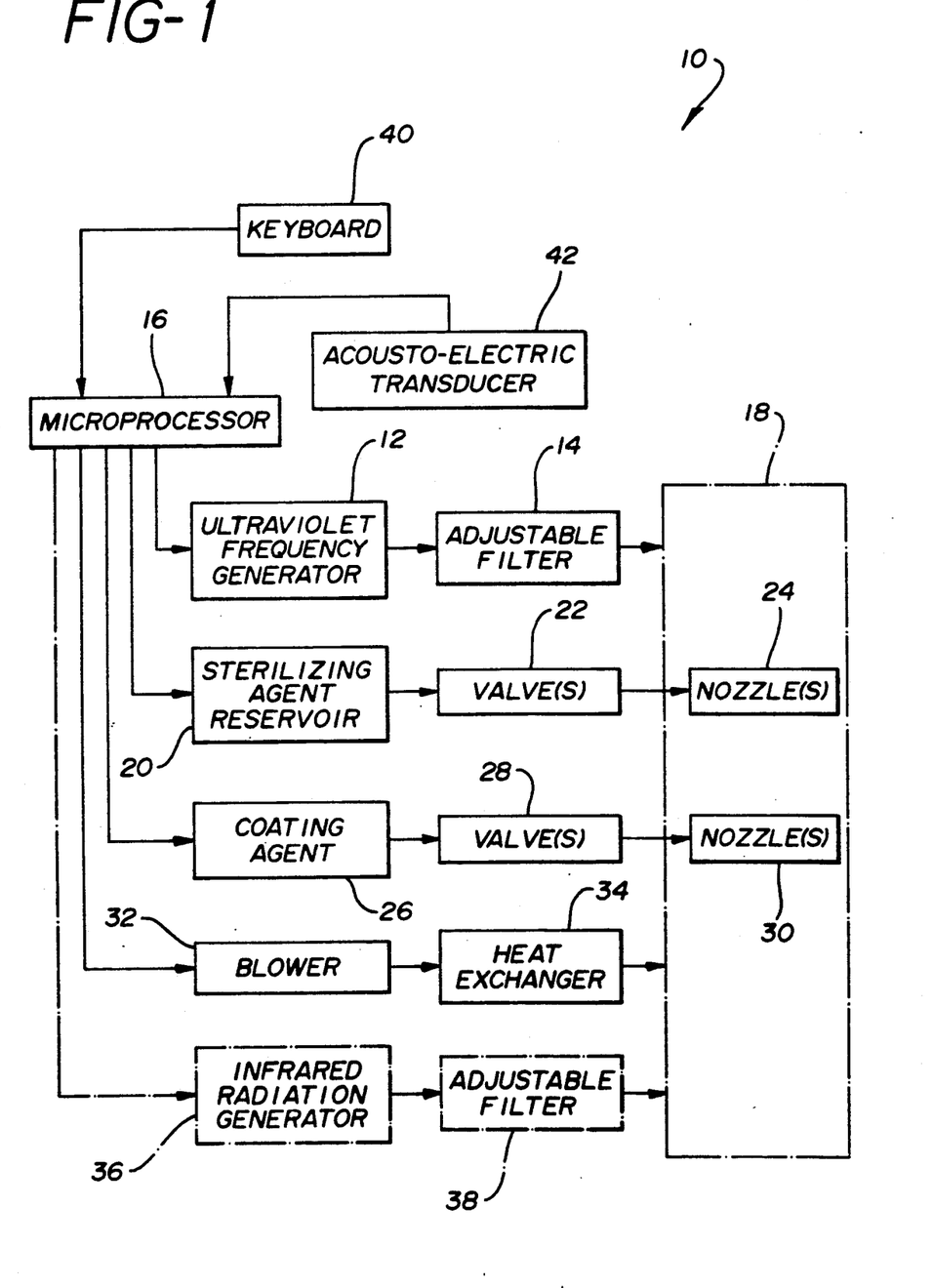
FIG. 1 is a block diagram of a sterilizing and coating apparatus in accordance with the present invention.
Figure 2:
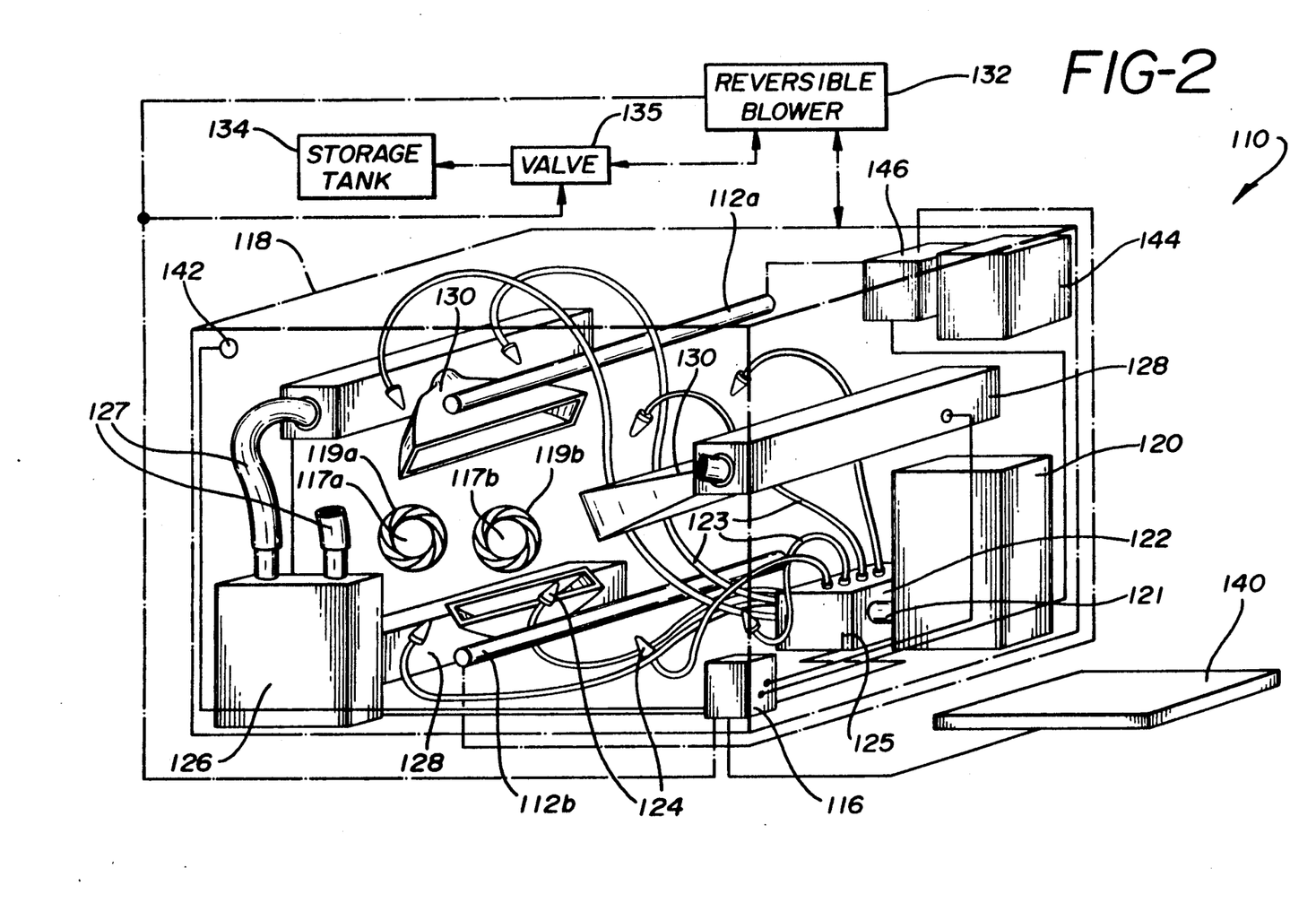
FIG. 2 is partially a schematic perspective view and partially a block diagram of a particular embodiment of a combined sterilizing and coating apparatus in accordance with the present invention.
Figure 5:
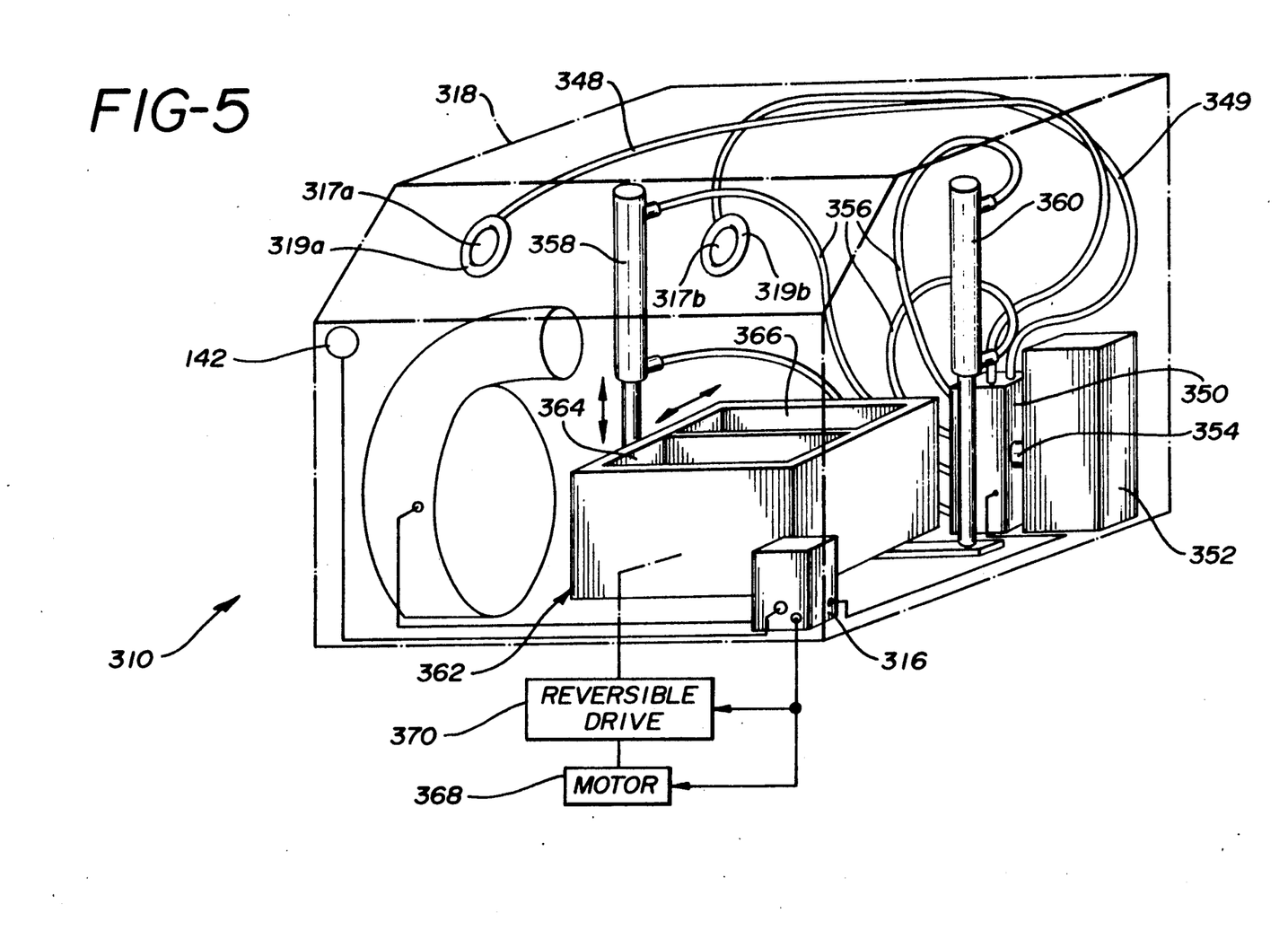
FIG. 5 is partially a schematic perspective view and partially a block diagram of yet another particular embodiment of a combined sterilizing and coating apparatus in accordance with the present invention.

As illustrated in FIG. 1, a combined sterilizing and coating apparatus 10 comprises a source or generator of ultraviolet radiation 12 having a frequency spectrum output which is adjustable, for example, by a filter 14 under the control of a microprocessor control unit 16. The electromagnetic energy output of radiation generator 12 and filter 14 is introduced into a sterilizing housing or chamber 18. As illustrated in FIGS. 2 and 5, a sterilizing chamber of an apparatus in accordance with the invention is provided with one or more openings for enabling the removable disposition inside the housing of an object (such as a person's hand) to be sterilized and/or provided with a protective covering (e.g., a glove-like protective layer).

The frequency spectrum of the output energy of radiation generator 12 is adjustable via filter 14 to facilitate optimization of the bacteriocidal capabilities of the radiation produced by generator 12.

Sterilizing and coating apparatus 10 also comprises a reservoir or storage unit 20 containing a fluidic sterilizing agent. Specifically, reservoir 20 may contain either a liquid disinfectant of any known type or a bacteriocidal gas. Ethylene oxide and propylene oxide are particularly effective in killing bacteria, viruses, spores and fungus. Inasmuch as these gases are dangerous to human beings, it is necessary to ensure that housing 18 is air tight and is provided with an evacuation system for removing the gaseous sterilant from the housing prior to removal of the object (e.g., hand) being sterilized.

Reservoir 20 has an output connected via a valve component 22 to at least one nozzle 24 inside housing 18. Valve 22 has a control input operatively connected to microprocessor 16, whereby the sterilizing agent is supplied to nozzle 24 in amounts and at times under the control of microprocessor 16.

Sterilizing and coating apparatus 10 further comprises a reservoir or storage unit 26 containing a coating agent. The coating agent takes the form of a liquid substance capable of forming on the surface of an object such as a person's hand a flexible membrane or coating layer. Preferably, the membrane or coating formed on an object by the liquid substance in reservoir 26 upon a deposition of the liquid substance on a surface of the object is at least partially liquid impermeable. Most preferably, the liquid substance is gas impermeable as well and forms a barrier to bacteria, viruses, spores and other microscopic life-forms. The liquid substance may be a vinyl or wax but is preferably a latex. In that event, reservoir 26 also contains a separate store of coagulant. The coagulant and the latex are then applied to the surface of the object in a predetermined sequence to effectuate the formation of a desired protective covering on an object inserted into housing 18.

Reservoir 26 has an output connected via a valve component 28 to at least one nozzle 30 inside housing 18. Valve 28 has a control input operatively connected to microprocessor 16, whereby the coating agent is supplied to nozzle 28 in amounts and at times under the control of microprocessor 16.

Sterilizing and coating apparatus 10 incorporates a blower 32 and a heat exchanger 34 each connected at control inputs to microprocessor 16. Blower 32 has an air output working into heat exchanger 34 which in turn has an air output extending to housing 18. Alternatively, or additionally, heat exchanger 34 may have independent access to the air in housing 18. Specifically, heat exchanger 34 may take the form of conventional heating coils.

In addition, sterilizing and coating apparatus 10 may include a source or generator of infrared radiation 36 for performing a drying function. Infrared radiation generator 36 and an adjustable filter 38 are operatively linked at control inputs to microprocessor 16, whereby the strength and frequency range of the emitted radiation are modifiable by a user.

Microprocessor 16 is connected at a pair of inputs to a keyboard 40 and an acousto-electric transducer or microphone 42. Microprocessor 16 is provided with software and ancillary hardware (not illustrated) for interpreting predetermined voice commands sensed by microphone 42. In response to the voice commands, microprocessor 16 initiates a sterilizing and/or coating operation in apparatus 10. For example, upon detecting the word "sterilize," microprocessor 16 energizes radiation generator 12 for a preselected time interval. The duration of the interval may be modified by a user via keyboard 40. The keyboard may also be used to instruct microprocessor 16 as to the desired strength and frequency of the sterilizing radiation. In response to such instructions, microprocessor 16 transmits a signal to filter 1, modifying the operation thereof.

Upon terminating the generation of the bacteriocidal ultraviolet radiation, microprocessor 16 operates valve(s) 22 to introduce the liquid or gaseous sterilizing agent into housing 18 from reservoir 20. This sterilizing step may again have a duration preset via keyboard 40. In addition, the rate at which the sterilizing agent is injected into housing 18 may be varied by microprocessor 16 in response to user input.

Upon terminating the introduction of sterilizing agent into housing 18, microprocessor 16 energizes blower 32 and, optionally, heat exchanger 34 to dry the object being sterilized. This step is particularly important if the sterilizing agent is a liquid. If the sterilizing agent is a gas, blower 32 is energized in a reverse direction by microprocessor 16 to evacuate housing 18 of the bacteriocidal gas.

Upon the drying and/or removal of the sterilizing agent from housing 18, microprocessor 16 opens valve(s) 28 to deposit via nozzle(s) 30 a liquid coating agent from reservoir 26 onto the sterilized object. Microprocessor 16 is programmed to close valve(s) 28 after a predetermined period and to simultaneously energize blower 3 and/or heat exchanger 34 to dry and solidify the deposited coating material. Microprocessor 16 may then implement several additional deposition and drying cycles, each cycle serving to place a fine layer of the coating material on the sterilized object. After several such cycles, a substantial protective covering has been deposited on the object. It is to be noted that the deposition and drying cycles are advantageously rapid to minimize the time the object is disposed in housing 18.

It is to be noted that the radiation generators 12 and 36 may function in part to cure the coating material upon the application thereof to the surface of the sterilized object.

As illustrated in FIG. 2, another combined sterilizing and coating apparatus 110 in accordance with the present invention comprises a sterilizing chamber or housing 118 encasing a pair of ultraviolet radiation tubes 112a and 112b having a frequency spectrum output which is adjustable under the control of a microprocessor control unit 116. Ultraviolet radiation tubes are energized with power from a transformer 144 or other source via a control unit 14 responsive to microprocessor 116.

Sterilizing chamber or housing 118 is provided with a pair of openings 117a and 117b for enabling the removable disposition in housing 118 of a person's hands for being sterilized and/or for being provided with a protective covering, i.e., a pairs of glove-like protective membranes.

Openings 117a and 117b are provided about their peripheries with respective inflatable cuffs 119a and 119b (alternatively, iris mechanisms or other devices) for sealing the openings about a person's wrists upon insertion of the person's hands through the openings. Inflatable cuffs 119a and 119b are connected to a pressure source (not illustrated) via a valve control (not illustrated) operated by microprocessor 116.

Sterilizing and coating apparatus 110 also comprises a reservoir or storage unit 120 containing a fluidic sterilizing agent. Specifically, reservoir 120 may contain either a liquid disinfectant of any known type or a bacteriocidal gas such as ethylene oxide and propylene oxide. Housing 118 is sealed to prevent the escape of the gases and is provided with a reversible blower 132 for evacuating housing 118 upon the completion of a sterilization procedure. Cuffs 119a and 119b remain closed about the person's wrists until the housing has been completely evacuated. Blower 132 has an air output extending to a storage tank 134 via a valve component 135.

Reservoir 120 has an output line 121 connected to a valve unit 122 which in turn is connected via hoses 123 to at least a plurality of nozzles 124. Valve unit 122 has a control input 125 operatively connected to microprocessor 116, whereby the sterilizing agent is supplied to nozzles 124 in controlled amounts and during intervals of preselected durations.

Sterilizing and coating apparatus 110 further comprises a reservoir or storage unit 126 containing a coating agent. As described hereinabove, the coating agent takes the form of a liquid or other substance capable of forming on the surfaces of person's hands a flexible membrane or coating layer. Most preferably, the formed membrane is gas impermeable and forms a barrier to bacteria, viruses, spores and other microscopic life-forms. The liquid substance may be a vinyl or wax but is preferably a latex. In that event, reservoir 126 also contains a separate store of coagulant. The coagulant and the latex are then applied to the surface of the object in a predetermined sequence under the control of microprocessor 116 to effectuate the formation of a desired protective covering on the person's hands upon insertion thereof into housing 118 via openings 117a and 117b.

Reservoir 126 has a output hoses 127 connected to valve units 128 in turn provided with respective nozzles 130. Valve units 128 have control inputs operatively connected to microprocessor 116, whereby the coating agent in reservoir 126 is supplied to nozzles 130 at predetermined rates and during intervals with durations controlled by microprocessor 116.

Microprocessor 116 is connected at a pair of inputs to a keyboard 140 and an acousto-electric transducer or microphone 142. Microprocessor 116 is provided with software and ancillary hardware (not illustrated) for interpreting predetermined voice commands sensed by microphone 142. In response to the voice commands, microprocessor 116 initiates a sterilizing and/or coating operation in apparatus 110. For example, upon detecting the word "sterilize," microprocessor 116 operates control unit 146 to energize ultraviolet radiation tubes 112a and 112b for a preselected time interval. The duration of the interval may be modified by a user via keyboard 140. The keyboard may also be used to instruct microprocessor 116 as to the desired strength and frequency of the sterilizing radiation. In response to such instructions, microprocessor 116 transmits a signal to control unit 146 and/or to a filter (not illustrated), modifying the operation thereof.

Upon terminating the generation of the bacteriocidal ultraviolet radiation, microprocessor 116 operates valve unit 122 to introduce the liquid or gaseous sterilizing agent into housing 118 from reservoir 120. This sterilizing step may again have a duration preset via keyboard 140. In addition, the rate at which the sterilizing agent is injected into housing 118 may be varied by microprocessor 116 in response to user input.

Upon terminating the introduction of sterilizing agent into housing 118, microprocessor 116 energizes blower 132 to dry the person's hands. This step is particularly important if the sterilizing agent is a liquid. If the sterilizing agent is a gas, blower 132 is energized in a reverse direction by microprocessor 116 to evacuate housing 118 of the bacteriocidal gas.

Upon the drying and/or removal of the sterilizing agent from housing 118, microprocessor 116 operates valve units 128 to deposit via respective nozzles 130 a liquid coating agent from reservoir 126 onto the person's hands. Microprocessor 116 is programmed to close the valves in units 28 after a predetermined period and to simultaneously energize blower 132 and/or a heat exchanger (not shown) to dry and solidify the deposited coating material. Microprocessor 116 may then implement several additional deposition and drying cycles, each cycle serving to place a fine layer of the coating material on the person's hands. After several such cycles, a substantial protective covering has been deposited on the hands. It is to be noted that the deposition and drying cycles are advantageously rapid to minimize the time the hands are disposed in housing 118.

It is to be noted that the radiation generators 12 and 36 may function in part to cure the coating material upon the application thereof to the hands.

Figure 3:
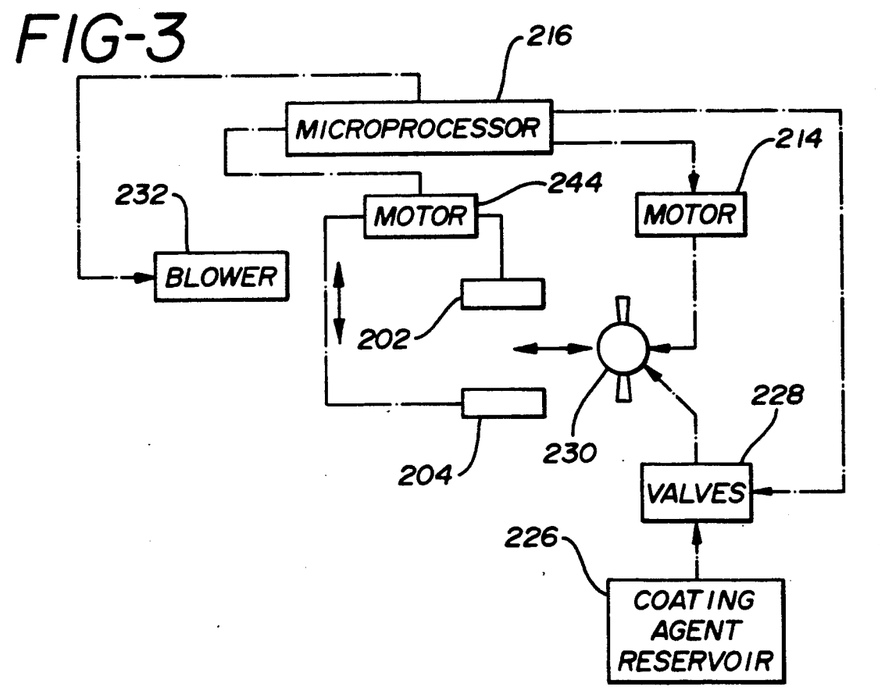
FIG. 3 is essentially a block diagram of portions of another particular embodiment of a combined sterilizing and coating apparatus in accordance with the present invention.
Figure 4:
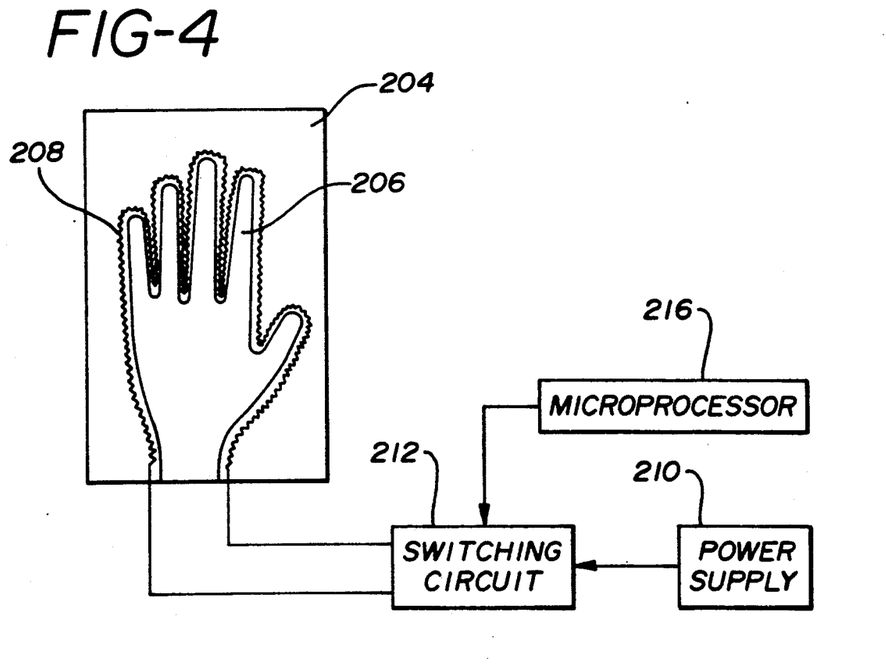
FIG. 4 includes a block diagram of other components of the combined sterilizing and coating apparatus of FIG. 3, as well as a schematic front elevational view of a component of the combined sterilizing and coating apparatus shown in FIG. 3.

In yet another embodiment of the present invention, shown in part in FIGS. 3 and 4, a glove is applied to a person's hand via a pair of mold halves 202 and 204. Mold half 204, corresponding to the lower half of a person's left hand, is illustrated in top view in FIG. 4. The mold half includes a depression or recess 206 in the form of a person's hand. Embedded in the material of the mold half, around the edges of recess 206 is a heating circuit 208. Circuit 208 is connectable to a power supply 210 via a switching circuit 212 operated under the control of a microprocessor 216. Prior to forming the glove, mold halves 202 and 204 are separated from one another as shown in FIG. 3. Microprocessor 216 energizes a motor 214 to move a nozzle assembly 230 between mold halves 202 and 204. Upon the disposition of nozzle assembly 230 at a preselected position between the mold halves, microprocessor 216 opens a valve 228 to allow a stream of coating agent to flow from a reservoir 226 through valve assembly 230 onto the surfaces of hand-shaped recesses 206 (only shown in FIG. 4) in the opposing faces of mold halves 202 and 204. Microprocessor 216 then operates a blower 232 to dry the deposited coating agent. As discussed hereinabove, several spraying and drying cycles may be implemented in order to effectively form glove halves in the recesses 206 of mold halves 202 and 204.

The surface of recess 206 is preferably coated with a layer of a material such as polytetrafluoroethylene designed to minimize sticking while yet enabling the deposition of coating agent to form a membrane layer on the recess surface. As discussed hereinabove, the spraying and drying cycles may include alternate spraying of coagulant and latex. The coagulant and latex may be sprayed through the same valve assembly 230, under the control of microporcessor 216, or alternatively may involve respective valve assemblies alternately moved in and out of the space between mold halves 202 and 204. Generally, conventional substances and techniques presently used in commercial glove making processes may be used to form the glove halves in the apparatus of FIGS. 3 and 4. As discussed hereinabove with reference to FIG. 2, a gloving apparatus as schematically depicted in FIGS. 3 and 4 is advantageously provided with a reversible blower for evacuating the housing chamber of gaseous materials prior to the insertion of a perons' hands. The housing chamber is completely sealed, e.g. by movable shuttes or doors, during the spraying operations.

Upon the insertion of a person's hands into a housing (not illustrated) and the detection of a "begin" command, microprocessor 216 operates a motor 244 to shift mold halves 202 and 204 towards one another about one of the person's hands. Two pairs of mold halves are preferably provided, one pair for each hand. Microprocessor 216 then shifts the mold halves to enclose both of the hands.

The shifting of the mold halves preferably, but not necessarily, succeeds a sterilization procedure as described above. The glove forming operations may then be initiated automatically by microprocessor 216 or, alternatively, only in response to a specific voice command. It is thus within the contemplation of the instant invention that the glove forming operation take place independently, without a sterilization step.

Upon the closure of mold halves 202 and 204 about a respective hand, microprocessor 216 closes switching circuit 212 to enable the flow of current through heating circuit 208. The heat generated by circuit 208 may be sufficiently swift and localized to prevent damage or pain to the hand. Cooling means may be provided for alternating with the energization of the heating coils to eliminate undesirable effects thereof. In a particular form of this embodiment of the invention, a glove may be formed with a small rib resulting from the joining of two glove halves to one another about their peripheries which are pressed between mold halves 202 and 204 upon the closure thereof.

FIG. 5 depicts coating and drying portions of a sterilizing and coating apparatus 310 in accordance with the invention. Sterilizing and coating apparatus 310 includes a housing 318 provided with a pair of openings 317a and 317b in turn provided around their edges with respective inflatable cuffs 319a and 319b for closing the openings about the wrists of a person's arms upon insertion of the person's hands through the openings. Inflatable cuffs 319a and 319b are coupled via respective hoses 348 and 349 to a valve unit 350 connected to a source 352 of pressurized air or other fluid via a line 354. Valve unit 350 is operated by a microprocessor 316 to pressurize and depressurize cuffs 319a and 319b to close and open them at the start and finish of a sterilizing and/or coating procedure.

Valve unit 350 is connected via additional hoses 356 to a pair of pneumatic cylinders 358 and 360, whereby microprocessor 316 controls the upward and downward motion of a storage member 362 having a pair of cells or receptacles 364 and 366 respectively holding a coagulant (e.g., a salt such as zinc nitrate) and liquid latex. Forward and backward motion of storage member 362 is controlled by microprocessor 316 via a motor 368 and a reversible transmission 370 operatively connected to the storage member. Upon detecting a voice command via a microphone 342 or, alternatively, at a predetermined time in an operation cycle, microprocessor 316 energizes motor 368 and operates transmission 370 to position receptacle 364 under hands (not shown) which have been inserted through openings 317a and 317b and about which cuffs 319a and 319b have been inflated. Microprocessor 216 then activates valve u it 350 to raise storage member 362 via pneumatic cylinders 358 and 360 so that the hands are immersed in the coagulant. After a predetermined period, microprocessor 316 operates valve unit 350 to lower storage member 362, operates motor 368 and transmission 370 to shift storage member 362 so that receptacle 366 is under the hands, and again operates valve unit 350 to raise storage member 362 so that the hands are immersed in the liquid latex. The foregoing steps may then be repeated to immerse the hands again in the coagulant. During the immersion process, or at predetermined stages thereof, microprocessor 316 energizes a blower 332 for facilitating drying or for evacuating housing 318. Housing 318 also contains irradiation equipment and sterilizing devices such as described hereinabove with reference to FIGS. 1 and 2. These equipment and devices have been omitted from FIG. 5 for purposes of clarity.

Figure 6:
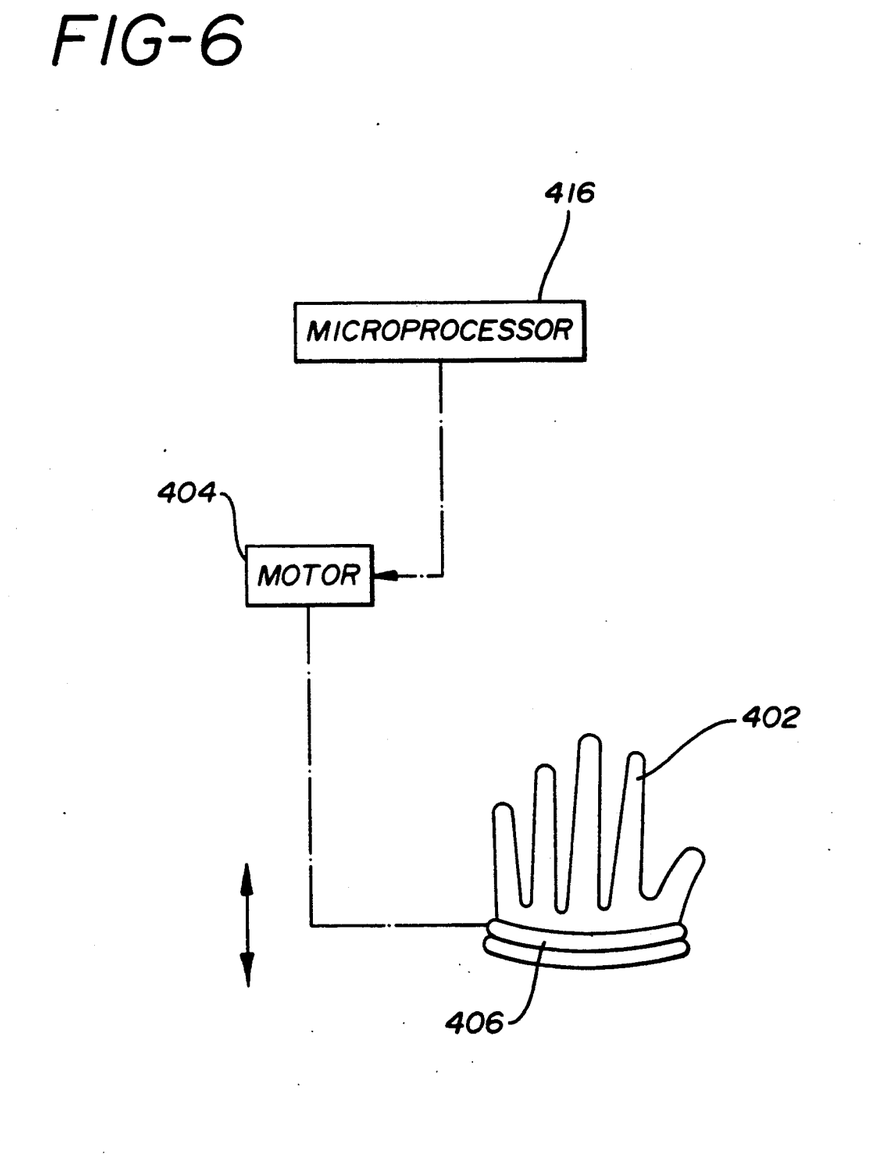
FIG. 6 is partially a block diagram and partially a perspective view of selected components of a further embodiment of a combined sterilizing and coating apparatus in accordance with the present invention.

As depicted schematically in FIG. 6, in another embodiment of the present invention, a series of preformed gloves 402 (only one shown in the drawing) are provided in a housing (not shown). The preformed gloves 402 are rolled up to the finger tips to facilitate insertion of the fingers of a person's hands into the gloves or, alternatively, for facilitating the automatic placement of the rolled up glove on the person's finger tips. Under the control of a microprocessor 416, a drive 404 moves a flexible, expandable ring 406 in a direction from the fingertips towards the wrist of a hand which has been inserted into the apparatus. That motion of the ring unrolls the rolled up glove onto the hand and lower arm. After ring 406 has been moved a predetermined distance, corresponding to the length of glove 402 in an unrolled state, the ring is expanded (e.g., by automatically opening a clasp or hook) and then retracted back along the length of the person's arm and past the finger tips. The hands may then be removed from the gloving apparatus.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A sterilization apparatus comprising:
   a housing provided with an opening through which an object may be inserted;
   first means at least partially inside said housing and connected thereto for irradiating with bacteriocidal radiation an object inserted into said housing through said opening;
   second means at least partially inside said housing and connected thereto for applying to the inserted object a sterilizing agent;
   third means at least partially inside said housing and connected thereto for applying to the inserted object a protective covering; and
   means operatively connected to said first means, said second means, and said third means for controlling and determining the activation of said first means, said second means, and said third means.

2. The apparatus defined in claim 1 wherein said first means includes means for generating and emitting ultraviolet radiation.

3. The apparatus defined in claim 2 wherein said first means further includes means operatively connected to said means for generating and emitting ultraviolet radiation for modifying the frequency and intensity of said ultraviolet radiation.

4. The system defined in claim 1 wherein said sterilizing agent is a liquid containing a bacteriocidal substance.

5. The apparatus defined in claim 4 wherein said second means includes means for spraying said liquid on said object.

6. The apparatus defined in claim 1 wherein said sterilizing agent is gaseous.

7. The apparatus defined in claim 1 wherein said third means includes means for applying to the inserted object a liquid substance which upon drying solidifies into a thin flexible film, further comprising means at least partially inside said housing for drying said liquid substance upon application thereof to the inserted object.

8. The apparatus defined in claim 7 wherein said third means includes means for spraying said liquid substance on the inserted object.

9. The apparatus defined in claim 7 wherein said third means includes a container inside said housing for holding said liquid substance to enable manual immersion of said object into said liquid substance.

10. The apparatus defined in claim 7 wherein said means for drying includes a blower.

11. The apparatus defined in claim 7 wherein said means for drying includes a heating device.

12. The apparatus defined in claim 7 wherein said means for drying includes means for generating infrared radiation.

13. The apparatus defined in claim 7 wherein said means for controlling includes means for activating said first means, said second means, and said third means in a predetermined sequence.

14. The apparatus defined in claim 13 wherein said means for controlling includes means for activating said means for drying upon application of said sterilizing agent to said object and upon application of said liquid substance to said object.

15. The apparatus defined in claim 1 wherein said object is a hand, said third means including means for forming a pair of glove portions, means for positioning said glove portions about the inserted hand to substantially enclose said hand, and means for joining said glove portions to one another to form said protective covering.

16. The apparatus defined in claim 15 wherein said means for forming includes a pair of mold halves and means for depositing a coating of a substantially nonporous flexible material onto said mold halves, said means for positioning including means for moving said mold halves towards one another.

17. The apparatus defined in claim 1 wherein said object is a hand, said third means including means for storing a plurality of preformed gloves rolled up into opened configurations facilitating the insertion of hands into the gloves, said third means further including means for rolling the rolled up gloves down about a pair of hands upon insertion thereof into the rolled up gloves.

18. The apparatus defined in claim 17 wherein said preformed gloves are oversized, said third means further comprises means for heat shrinking one of the oversized gloves about a hand inserted thereinto.

19. The apparatus defined in claim 1 wherein said means for controlling is user responsive.

20. The apparatus defined in claim 19 wherein said means for controlling includes means for sensing spoken sounds, said means for controlling includes means for selectively activating said first means, said second means, and said third means in response to different spoken sounds.

21. The apparatus defined in claim 1 wherein said means for controlling includes means for activating said first means, said second means, and said third means in a predetermined sequence.

22. An apparatus for providing a glove about a hand, comprising:

a housing provided with an opening through which the hand may be inserted;

means at least partially inside said housing and connected thereto for applying to the inserted hand a protective covering in the form of a membrane impermeable to bacteria; and means operatively connected to said means for applying for controlling the activation of said means for applying.

23. The apparatus defined in claim 22 wherein said means for applying includes means for coating and inserted hand with a liquid substance which upon drying solidifies into a thin flexible membrane, further comprising means at least partially inside said housing and connected thereto for drying said liquid substance upon application thereof to the inserted hand.

24. The apparatus defined in claim 23 wherein said means for coating includes means for spraying said liquid substance on the inserted hand.

25. The apparatus defined in claim 23 wherein said means for coating includes a container inside said housing for holding said liquid substance to enable immersion of said hand into said liquid substance.

26. The apparatus defined in claim 23 wherein said means for drying includes a blower.

27. The apparatus defined in claim 23 wherein said means for drying includes a heating device.

28. The apparatus defined in claim 23 wherein said means for drying includes means for generating infrared radiation.

29. The apparatus defined in claim 23 wherein said means for controlling includes means for activating said means for coating and said means for drying in a predetermined sequence.

30. The apparatus defined in claim 22 wherein said means for applying includes means for forming a pair of glove portions, means for positioning said glove portions about the inserted hand to substantially enclose said hand, and means for joining said glove portions to one another to form said protective covering.

31. The apparatus defined in claim 30 wherein said means for forming includes a pair of mold halves and means for depositing a coating of a substantially nonporous flexible material onto said mold halves, said means for positioning including means for moving said mold halves towards one another.

32. The apparatus defined in claim 22 wherein said means for applying includes means for storing a plurality of preformed gloves rolled up into opened configurations facilitating the insertion of hands into the gloves, said means for applying further including means for rolling a rolled up glove down about a hand upon insertion thereof into the rolled up glove.

33. The apparatus defined in claim 32 wherein said preformed gloves are oversized, said means for applying further comprising means for heat shrinking one of the oversized gloves about a hand inserted thereinto.

34. The apparatus defined in claim 22 wherein said means for controlling is user responsive.

35. The apparatus defined in claim 34 wherein said means for controlling includes means for sensing spoken sounds.

36. A sterilization apparatus comprising:

a housing provided with an opening through which an object may be inserted;

first means at least partially inside said housing and connected thereto for irradiating with bacteriocidal radiation an object inserted into said housing through said opening;

second means at least partially inside said housing and connected thereto for applying to the inserted object a sterilizing agent; and means operatively connected to said first means and said second means for controlling and determining the activation of said first means and said second means.

37. The apparatus defined in claim 36 wherein said first means includes means for generating and emitting ultraviolet radiation.

38. The apparatus defined in claim 37 wherein said first means further includes means for modifying the frequency and intensity of said ultraviolet radiation.

39. The apparatus defined in claim 36 wherein said sterilizing agent is an atomized liquid containing a bacteriocidal substance.

40. The apparatus defined in claim 39 wherein said second means includes means for spraying said liquid on said object.

41. The apparatus defined in claim 36 wherein said sterilizing agent is gaseous.

42. The apparatus defined in claim 36, further comprising means disposed at least partially inside said housing and connected thereto for drying the object upon application of the sterilizing agent thereto.

43. A sterilization apparatus comprising:

a housing provided with an opening through which an object may be inserted;

first means at least partially inside said housing and connected thereto for irradiating with bacteriocidal radiation an object inserted into said housing through said opening;

second means at least partially inside said housing and connected thereto for applying to the inserted object a protective covering; and means operatively connected to said first means and said second means for controlling and determining the activation of said first means and said second means.

44. The apparatus defined in claim 43 wherein said first means includes means for generating and emitting ultraviolet radiation.

45. The apparatus defined in claim 44 wherein said first means further includes means operatively connected to said means for generating and emitting ultraviolet radiation for modifying the frequency and intensity of said ultraviolet radiation.

46. The apparatus defined in claim 43 wherein said second means includes means for coating the inserted object with a liquid substance which upon drying solidifies into a thin flexible film, further comprising means at least partially inside said housing for drying said liquid substance upon application thereof to the inserted object.

47. The apparatus defined in claim 46 wherein said second means includes means for spraying said liquid substance on the inserted object.

48. The apparatus defined in claim 46 wherein said second means includes a container inside said housing for holding said liquid substance to enable manual immersion of said object into said liquid substance.

49. The apparatus defined in claim 43 wherein said object is a hand, said second means including means for forming a pair of glove portions, means for positioning said glove portions about the inserted hand to substantially enclose said hand, and means for joining said glove portions to one another to form said protective covering.

50. The apparatus defined in claim 49 wherein said means for forming includes a pair of mold halves and means for depositing a coating of a substantially nonporous flexible material onto said mold halves, said means for positioning including means for moving said mold halves towards one another.

51. The apparatus defined in claim 43 wherein said object is a hand, said second means including means for storing a plurality of preformed gloves rolled up into opened configurations facilitating the insertion of hands into the gloves, said second means further including means for rolling the rolled up gloves down about a pair of hands upon insertion thereof into the rolled up gloves.

52. A sterilization apparatus comprising:

a housing provided with an opening through which an object may be inserted;

first means at least partially inside said housing and connected thereto for applying to the inserted object a sterilizing agent;

second means at least partially inside said housing and connected thereto for applying to the inserted object a protective covering; and means operatively connected to said first means and said second means for controlling and determining the activation of said first means and said second means.

53. The apparatus defined in claim 52 wherein said sterilizing agent is an atomized liquid containing a bacteriocidal substance.

54. The apparatus defined in claim 53 wherein said first means includes means for spraying said liquid on said object.

55. The apparatus defined in claim 52 wherein said sterilizing agent is gaseous.

56. The apparatus defined in claim 52, further comprising means for drying the object upon application of said sterilizing agent thereto.

57. The apparatus defined in claim 52 wherein said second means includes means for coating the inserted object with a liquid substance which upon drying solidifies into a thin flexible film, further comprising means at least partially inside said housing for drying said liquid substance upon application thereof to the inserted object.

58. The apparatus defined in claim 57 wherein said second means includes means for spraying said liquid substance on the inserted object.

59. The apparatus defined in claim 57 wherein said second means includes a container inside said housing for holding said liquid substance to enable manual immersion of said object into said liquid substance.

60. The apparatus defined in claim 52 wherein said object is a hand, said second means including means for forming a pair of glove portions, means for positioning said glove portions about the inserted hand to substantially enclose said hand, and means for joining said glove portions to one another to form said protective covering.

61. The apparatus defined in claim 60 wherein said means for forming includes a pair of mold halves and means for depositing a coating of a substantially nonporous flexible material onto said mold halves, said means for positioning including means for moving said mold halves towards one another.

62. The apparatus defined in claim 52 wherein said object is a hand, said second means including means for storing a plurality of preformed gloves rolled up into opened configurations facilitating the insertion of hands into the gloves, said second means further including means for rolling the rolled up gloves down about a pair of hands upon insertion thereof into the rolled up gloves.

* * * * *